(12) United States Patent
Heaps

(10) Patent No.: US 11,373,745 B1
(45) Date of Patent: Jun. 28, 2022

(54) AUTOMATIC MEDICATION DISPENSER

(71) Applicant: Richard Heaps, Port Richey, FL (US)

(72) Inventor: Richard Heaps, Port Richey, FL (US)

(*) Notice: Subject to any disclaimer, the term of this patent is extended or adjusted under 35 U.S.C. 154(b) by 146 days.

(21) Appl. No.: 16/863,636

(22) Filed: Apr. 30, 2020

(51) Int. Cl.
| | | |
|---|---|---|
| *G16H 20/13* | (2018.01) | |
| *A61J 7/00* | (2006.01) | |
| *A61J 7/04* | (2006.01) | |
| *G16H 40/67* | (2018.01) | |
| *G08B 3/10* | (2006.01) | |
| *H04N 5/225* | (2006.01) | |
| *G06F 3/02* | (2006.01) | |
| *H04R 1/02* | (2006.01) | |
| *G06V 40/13* | (2022.01) | |
| *G06V 40/12* | (2022.01) | |

(52) U.S. Cl.
CPC ............ *G16H 20/13* (2018.01); *A61J 7/0076* (2013.01); *A61J 7/0481* (2013.01); *G06F 3/02* (2013.01); *G06V 40/13* (2022.01); *G06V 40/1365* (2022.01); *G08B 3/10* (2013.01); *G16H 40/67* (2018.01); *H04N 5/2253* (2013.01); *H04R 1/028* (2013.01)

(58) Field of Classification Search
CPC ....... G16H 20/13; G16H 40/67; A61J 7/0076; A61J 7/0481; G08B 3/10; G06K 9/00087; G06K 9/00013; H04N 5/2253; G06F 3/02; H04R 1/028
See application file for complete search history.

(56) References Cited

U.S. PATENT DOCUMENTS

| | | | |
|---|---|---|---|
| 5,522,525 A | 6/1996 | McLaughlin et al. | |
| 6,210,329 B1* | 4/2001 | Christmas | A61B 50/31 600/437 |
| 7,885,725 B2* | 2/2011 | Dunn | G07F 9/02 700/237 |
| 8,271,128 B1* | 9/2012 | Schultz | G16H 20/13 700/236 |
| 8,326,455 B2* | 12/2012 | Dunn | G07F 9/02 700/237 |
| 9,913,778 B2 | 3/2018 | Dvorak et al. | |
| 2007/0156282 A1* | 7/2007 | Dunn | G07F 9/02 700/244 |
| 2011/0166700 A1* | 7/2011 | Dunn | A61J 7/0076 700/237 |
| 2012/0056000 A1* | 3/2012 | Shores | A61J 7/0418 235/492 |
| 2015/0119652 A1* | 4/2015 | Hyde | G16H 40/67 600/301 |

(Continued)

*Primary Examiner* — Michael Collins
(74) *Attorney, Agent, or Firm* — Sanchelima & Associates, P.A.; Christian Sanchelima; Jesus Sanchelima

(57) ABSTRACT

An automatic medication dispenser is disclosed herein. The automated prescription medication dispensing machine includes a container for housing multiple medication pills. The container has a programmable dispensing system, an audible reminder alert, a biometric sensor and a proximity alarm. Additionally, the dispenser can be programmed to dispense a prescribed dosage at a prescribed time or interval and can only be activated using a biometric fingerprint scanner. Furthermore, the system has an audible reminder alarm for a patient. If the machine is moved from a set location an audible alert is activated to prevent the dispenser from being stolen.

3 Claims, 5 Drawing Sheets

(56) References Cited

U.S. PATENT DOCUMENTS

| | | | |
|---|---|---|---|
| 2016/0022543 A1* | 1/2016 | Deeter | A61J 7/0427 |
| | | | 221/1 |
| 2016/0324727 A1* | 11/2016 | Waugh | G16H 20/13 |
| 2018/0008498 A1* | 1/2018 | Sciacchitano | E05B 65/462 |
| 2018/0039756 A1* | 2/2018 | Phipps | G06F 21/6245 |
| 2019/0240114 A1* | 8/2019 | Arric | A61J 7/0007 |

* cited by examiner

AUTOMATIC MEDICATION DISPENSER

BACKGROUND OF THE INVENTION

1. Field of the Invention

The present invention relates to a medication dispenser and, more particularly, to an automatic medication dispenser that provides an audible alert to a user to remind them to take their medication and then authenticates the user through a biometric sensor.

2. Description of the Related Art

Several designs for a medication dispenser have been designed in the past. None of them, however, include an automated prescription medication dispensing machine including a container for housing multiple medication pills. The container has a programmable dispensing system, an audible reminder alert, a biometric sensor and a proximity alarm. Additionally, the dispenser can be programmed to dispense a prescribed dosage at a prescribed time or interval and can only be activated using a biometric fingerprint scanner. Furthermore, the system has an audible reminder alarm for a patient. If the machine is moved from a set location an audible alert is activated to prevent the dispenser from being stolen. The dispenser may also include a keyboard built into the front of the dispenser. The keyboard allows a user to directly program the device in order to set reminders and adjust dosages that are being provided by the dispenser. It is known that medication is often very expensive and a private matter for the lives of many people on sensitive medications. Individuals often have a need to protect their medication from being stolen and protect their privacy. Therefore, there is a need for an automatic medication dispenser that protects a user's medication and protects a user's privacy.

Applicant believes that a related reference corresponds to U.S. Pat. No. 9,913,778 issued for a secure personal medication dispenser which dispenses only a prescribed dosage at a prescribed time and can only be accessed using a biometric fingerprint scanner. Applicant believes that another related reference corresponds to U.S. Pat. No. 5,522,525 issued for a medication dispenser station for automatic dispensing of medication in accordance with a prescription schedule for a patient. However, the cited references differ from the present invention because they fail to disclose a programmable dispensing system with a proximity alarm that alerts a user when the dispenser is being transported under unauthorized means. Additionally, the present invention includes an audible alert that reminds a user to take their prescribed medication.

Other documents describing the closest subject matter provide for a number of more or less complicated features that fail to solve the problem in an efficient and economical way. None of these patents suggest the novel features of the present invention.

SUMMARY OF THE INVENTION

It is one of the objects of the present invention to provide an automatic medication dispenser that securely protects a user's medication in a container that is authenticated by a biometric scanner.

It is another object of this invention to provide an automatic medication dispenser that provides audible alerts to a user in order to remind them to take their medication.

It is still another object of the present invention to provide an automatic medication dispenser having a proximity alarm that provides an audible alert when the dispenser device is being stolen.

It is still another object of the present invention to provide an automatic medication dispenser which prevents individuals from becoming addicted to opioids.

It is yet another object of this invention to provide such a device that is inexpensive to implement and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Figure 1:
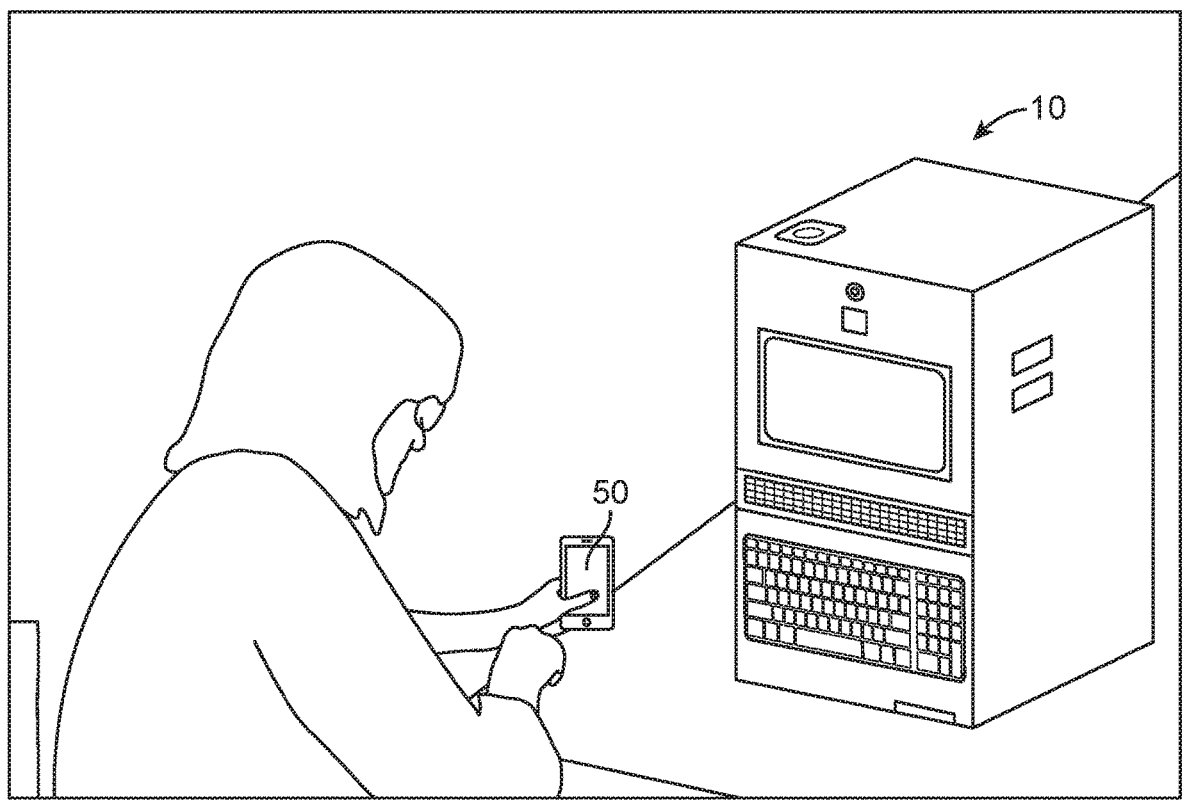
FIG. 1 represents an isometric operational view of an automatic medication dispenser 10 in accordance to an embodiment of the present invention.
Figure 2:
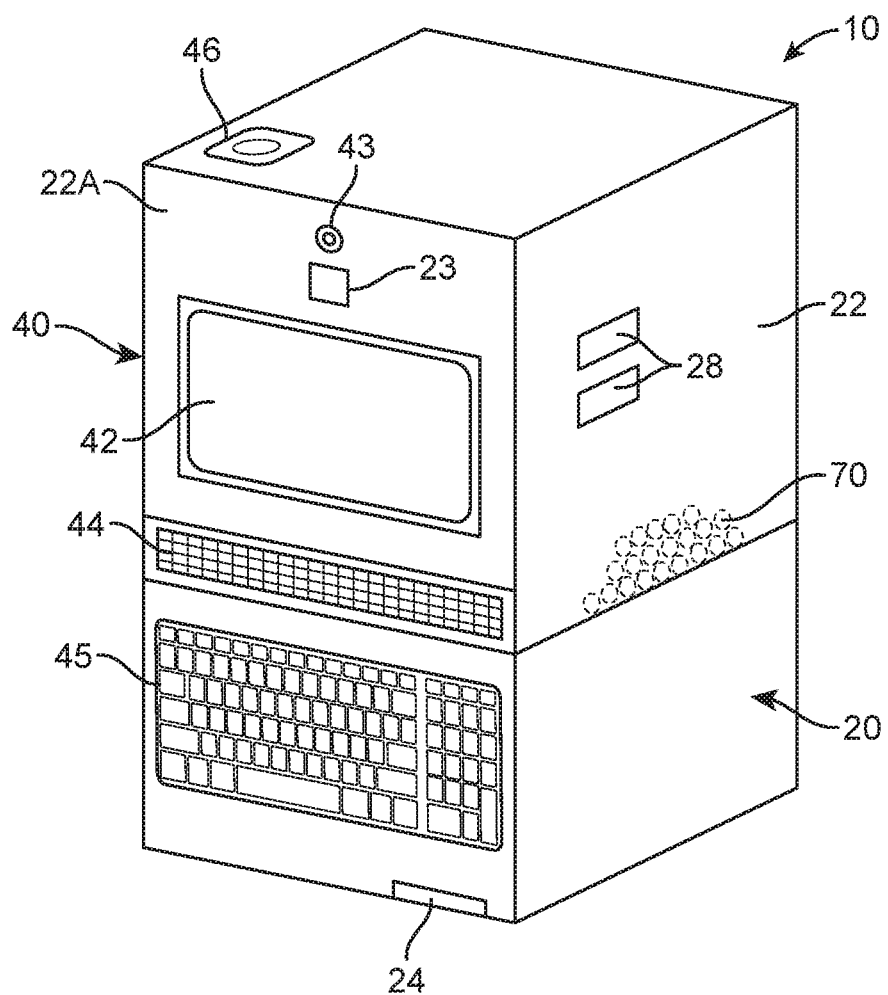
FIG. 2 shows an isometric view of automatic medication dispenser 10 depicting various components of housing assembly 20 and communication assembly 40 in accordance to an embodiment of the present invention.
Figure 3:
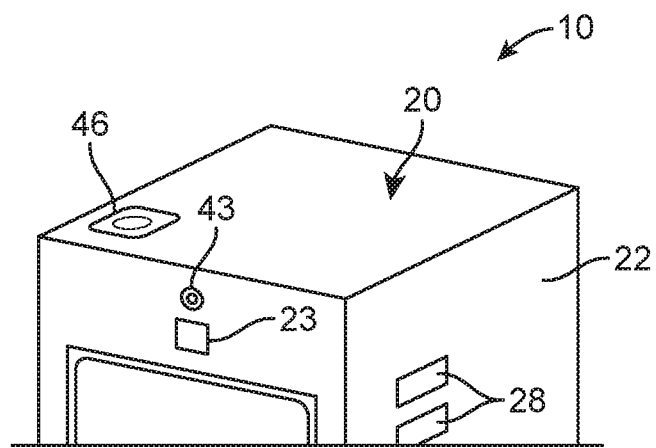
FIG. 3 illustrates an enlarged top isometric view of housing assembly 20 in accordance to an embodiment of the present invention.
Figure 4:
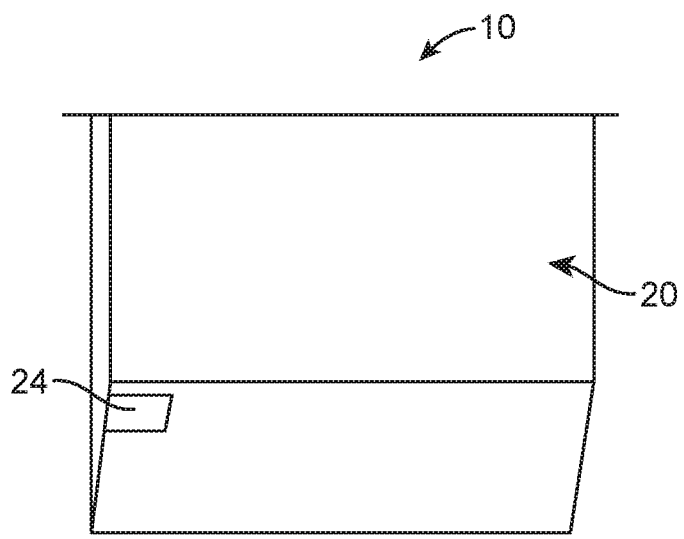
FIG. 4 is a representation of a bottom view of housing assembly 20 depicting a securable door 24 mounted thereon in accordance to an embodiment of the present invention.
Figure 5:
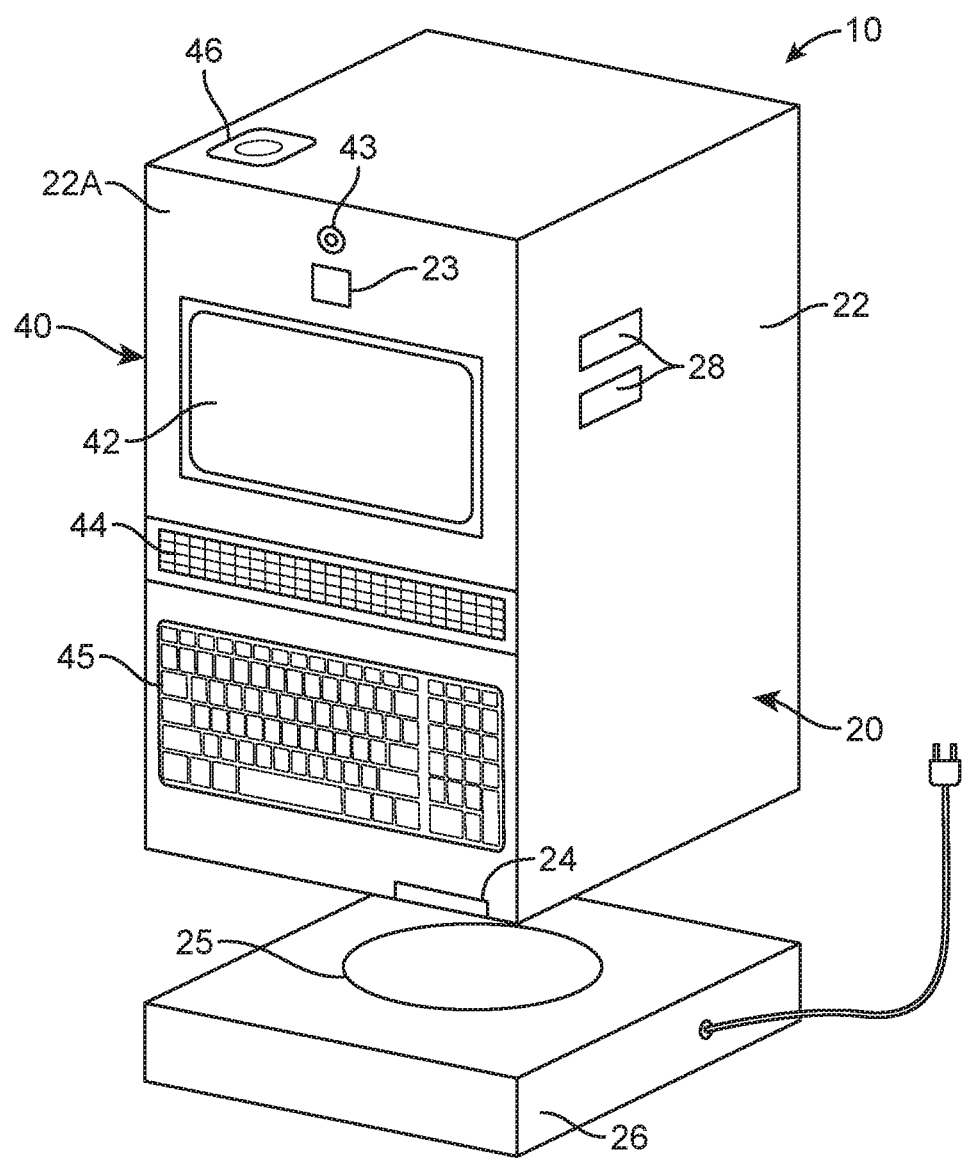
FIG. 5 shows an isometric exploded view of housing assembly 20 having a magnet 25 and a charging base 26 in accordance to an embodiment of the present invention.
Figure 6:
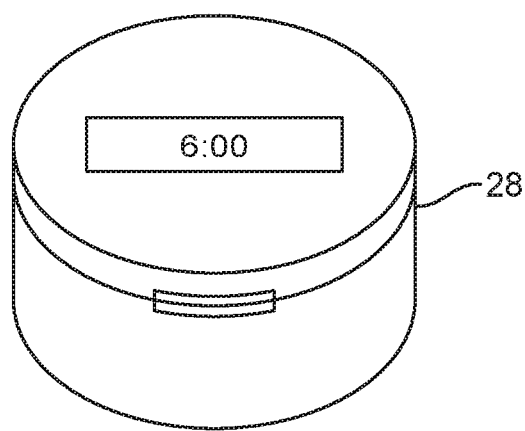
FIG. 6 illustrates an isometric view of portable pill dispenser 28 in accordance to an embodiment of the present invention.

Referring now to the drawings, where the present invention is generally referred to with numeral 10, it can be observed an automatic medication dispenser 10 which basically includes a housing assembly 20 and a communication assembly 40.

Housing assembly 20 includes a container 22 having a front end and an interior space. In one embodiment, container 22 has a cubic rectangular shape and includes a flat front face 22A. Other embodiments may feature a container 22 having other suitable shapes and sizes. Additionally, container 22 may be made of a durable material to be used for a long period of time. These materials may include metal, carbon fiber, plastic, and the like. Flat front face 22A may be defined as a portion of the front end of container 22 that is entirely flat and extends the entire front end of the container. Container 22 further includes an interior space having medication 70 stored therein. In one implementation, medication 70 is provided in the form of pills or capsules. Other implementations may feature medication 70 in additional forms and varieties such as bottles or bags. In the present embodiment, flat front face 22A includes opening 23 thereon. Opening 23 may be square in shape and located near a top edge of container 22. In the present implementation, opening 23 receives medication 70 that is being dispensed from the interior of container 22. Other embodiments may feature opening 23 of varying shapes and location on protruding sidewall 22A. A user may then remove medication 70 from opening 23 to be consumed. In one embodiment, medication 70 may be returned within container 22 if the medication 70 is not taken within a predetermined amount of time.

Housing assembly 20 further includes a securable door 24 located on a bottom end of container 22. In one embodiment, securable door 24 is square in shape and provided along a corner of the bottom end of container 22. Additionally, securable door 24 may be of a removable variety to provide access to an interior space within container 22. A user may then remove securable door 24 to then supply container 22 with the pills needed to order to use the device. Other embodiments of securable door 24 may include a hingedly attached cover or a cover having a locking mechanism. In another embodiment, securable door 24 may be locked to only be removed by an authorized physician or doctor to prevent a user to adding incorrect medication to the device. Container 22 may further include a magnet 25 that is coupled to a top end of a charging base 26. In one implementation, magnet 25 is a circular magnet located on a center portion of charging base 26 that securely couples to metal surfaces. Magnet 25 allows a user to secure the container 22 to charging base 26. In one implementation, charging base 26 is rectangular in shape and includes a power cord that is configured to be plugged into an outlet. Charging base 26 provides the necessary charge to a battery found within container 22 that powers various components of the automatic medication dispenser 10. Other embodiments of the present invention may feature a power plug built directly into the container 22 in order to omit the need of charging base 26.

Housing assembly further includes a portable pill dispenser 28 that may be mounted along the sidewall of container 22. In one embodiment, portable pill dispenser 28 is cylindrical in shape and inserted within a slot of container 22. Portable pill dispenser 28 is provided with a timer and a secure lock. In one implementation, portable pill dispenser 28 holds medication that is to be taken by a user in the event a user has to travel away from container 22. The timer may be set at a predetermined time such as 6 hours. Once the timer has ended, the lock of the portable pill dispenser 28 may release allowing a user to have access to the medication therein. This allows a user to effectively take their medication in the event where they will not have access to container 22. When portable pill dispenser 28 is mounted within container 22 it receives a charge therein which will power the lock and the timer for a predetermined amount of time.

Communication assembly 40 includes a screen 42 located on the front side of container 22. In one embodiment, screen 42 is a LED screen that is rectangular in shape. Other embodiments may include a screen 42 of the touch screen variety. In the present embodiment, screen 42 provides a user with important information regarding their medication 70. This may include information such as the prescription of the medication as well as a schedule of when the medication should be taken. Additionally, screen 42 may display information such as the amount of medication 70 that is currently within container 22. Screen 42 may further be used to provide a user with visual alerts to notify the user to take their prescribed medication. Communication assembly 40 further includes a camera 43 mounted above opening 23 near a top edge of container 22. In one implementation, camera 43 is a high definition camera that records visual media from the surrounding area of container 22. Automatic medication dispenser 10 is additionally configured to work in conjunction with a mobile device 50. In one embodiment, the visual media recorded by camera 43 is transmitted to mobile device 50. This may allow a family member or loved one of a user to observe the user while they take their medication from the automatic medication dispenser 10. In one embodiment, camera 43 also allows a physician to observe their patient on mobile device 50 while they take their prescribed medication.

Communication assembly 40 also includes a speaker 44 which may be located beneath screen 42. In one embodiment, speaker 44 is of a speaker bar variety that extends along the width of container 22. Furthermore, speaker 44 provides a user with an audible reminder alert and a proximity alarm that is broadcasted thereout. In one implementation, the audible reminder alert provides a user with audible reminders to take their medication. These audible reminders may be provided at specific scheduled times or intervals. In one embodiment, these times and intervals are programmed manually by a user into container 22. In another embodiment, these times and intervals may only be modified by an authorized physician with access to program automatic medication dispenser 10. The proximity alarm is provided to help a user prevent automatic medication dispenser 10 from being stolen. In one embodiment, this proximity alarm is actuated once container 22 is removed from a predetermined location by a user with unauthorized access. In another embodiment, the proximity alarm is actuated if the device is unable to be authenticated due to unauthorized access. The proximity alarm may be provided as a loud audible alarm sound that is broadcasted through speaker 44. Additionally, when the proximity alarm is activated, a notification is sent to a loved one mobile device notifying them of unauthorized access of the device. Furthermore, camera 23 is streamed to the loved one's mobile device for them to identify the unauthorized intruder and call the authorities to apprehend the intruder.

Communication assembly 40 may further include a keyboard 45 located near a bottom end of float front face 22A. In one embodiment, keyboard 45 is provided as a qwerty keyboard allowing a user to program various parameters of automatic medication dispenser 10. In another embodiment, keyboard 45 is provided as a keypad for a simpler configuration and allows a user to change various settings regarding automatic medication dispenser 10. Other embodiments of the present invention may omit keyboard 45 as it may not be a necessary function for some patients and users. Additionally, communication assembly 40 includes a biometric scanner 46 located on a top end of container 22. In one implementation, biometric scanner 46 may be provided as a fingerprint scanner that is located along the edge of the top end. Other implementations may feature other varieties of biometric scanners such as facial recognition and the like. Biometric scanner 46 is provided in order to authenticate a user attempting to utilize automatic medication dispenser 10 in order to obtain medication 70. In one embodiment, medication 70 is only dispensed once biometric scanner 46 has successfully authorized the correct user. If the user is unable to be authenticated, proximity alarm may then be actuated to notify surrounding individuals. Additionally, a notification may be sent to a user's mobile device 50 in order to further alert them of unauthorized access. In on embodiment, medication 70 is dispensed at a prescribed dosage and at a prescribed time or interval. A user may be unable to obtain medication that has not been prescribed. A user may also be unable to obtain the medication if the dispenser is authenticated at an incorrect time or interval. This disclosed system prevents individuals from becoming addicted to opioids by limiting their access to the prescribed medication and preventing other users from accessing the addictive medication.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A system for an automatic medication dispenser, comprising:
   a. a mobile device;
   b. a housing assembly including a container including a front side and having a cubic rectangular shape, wherein said front side is a flat front face, said container having an internal space containing medications in the form of pills therein, wherein said flat front face includes an opening near a top end, wherein said pills within said container are dispensed from said opening, wherein said container includes a bottom side having a securable door, wherein said securable door has a square shape and provides access to said internal space, said securable door configured to be locked by a user, wherein said bottom side of said container is received by a charging base having a power plug, wherein said charging base is rectangular in shape, wherein said charging base includes a magnet mounted on a top end, wherein said magnet is circular in shape and receives said container to be mounted thereon; and
   c. a communication assembly including a rectangular screen located on said front side configured to provide a user with information regarding their medication, a camera located above said opening near a top edge of said flat front face, wherein said camera broadcasts visual media to said mobile device, a speaker bar located below said screen to broadcast an audible reminder alert and a proximity alarm, wherein proximity alarm is actuated when said container is removed from a pre-determined location, a keyboard located on said flat front face near a bottom edge adapted to allow a user to program parameters of said communication assembly, a biometric scanner located on a top end of said container, wherein said biometric scanner is a finger print scanner, wherein said pills are dispensed only after said biometric scanner authenticates said user, wherein said pills are dispensed at a prescribed dosage and at a prescribed time or interval.

2. The system for an automatic medication dispenser of claim 1 wherein said container includes a portable pill dispenser mounted to a sidewall of said container.

3. The system for an automatic medication dispenser of claim 2 wherein said portable pill dispenser includes a timer and a lock.

* * * * *